US012727841B2

(12) United States Patent
Nabatame et al.

(10) Patent No.: US 12,727,841 B2

(45) Date of Patent: Sep. 8, 2026

(54) INFORMATION PROCESSING APPARATUS

(71) Applicant: CANON KABUSHIKI KAISHA, Tokyo (JP)

(72) Inventors: Takeo Nabatame, Otawara (JP); Hiroaki Miyazaki, Otawara (JP)

(73) Assignee: CANON KABUSHIKI KAISHA, Tokyo (JP)

(*) Notice: Subject to any disclaimer, the term of this patent is extended or adjusted under 35 U.S.C. 154(b) by 278 days.

(21) Appl. No.: 18/460,094

(22) Filed: Sep. 1, 2023

(65) Prior Publication Data

US 2024/0074723 A1 Mar. 7, 2024

(30) Foreign Application Priority Data

Sep. 5, 2022 (JP) ................................ 2022-140540

(51) Int. Cl.

*A61B 6/00* (2024.01)
*A61B 6/42* (2024.01)
*G01T 1/24* (2006.01)

(52) U.S. Cl.

CPC ............ *A61B 6/545* (2013.01); *A61B 6/4241* (2013.01); *A61B 6/482* (2013.01); *G01T 1/247* (2013.01)

(58) Field of Classification Search

CPC .............................. A61B 6/545; A61B 6/4241
See application file for complete search history.

(56) References Cited

U.S. PATENT DOCUMENTS 9,693,743 B2* 7/2017 Arakita ............... G01T 1/20182
10,451,568 B2* 10/2019 Moriyasu ............... G16H 50/20
2014/0023181 A1* 1/2014 Noshi .................... A61B 6/482 378/91
2015/0257722 A1 9/2015 Wang et al.
2015/0287193 A1 10/2015 Kato et al.
2017/0202531 A1* 7/2017 Nitta ........................ A61B 6/50
(Continued)

FOREIGN PATENT DOCUMENTS

JP 2006-101926 A 4/2006
JP 2014-138796 A 7/2014
(Continued)

OTHER PUBLICATIONS

Extended European Search Report Issued Jan. 25, 2024 in European Application 23195193.0, 6 pages.
(Continued)

*Primary Examiner* — David J Makiya

(74) *Attorney, Agent, or Firm* — Oblon, McClelland, Maier & Neustadt, L.L.P.

(57) ABSTRACT

An information processing apparatus according to the present embodiment sets an image generation condition for photon counting computed tomography (PCCT) imaging, the information processing apparatus comprising processing circuitry. The processing circuitry configured to receive an input which specifies a radiogram interpretation target, based on target-by-target setting information in which, for each radiogram interpretation target, energy range setting is defined which is related to an energy range meant for discriminating photons originating from X-rays that have passed through a subject, obtain energy range setting corresponding to the radiogram interpretation target that is received, and set the energy range setting that is obtained.

9 Claims, 5 Drawing Sheets

(56) References Cited

U.S. PATENT DOCUMENTS

| | | | | |
|---|---|---|---|---|
| 2018/0038969 | A1 | 2/2018 | Mccollough et al. | |
| 2018/0068464 | A1* | 3/2018 | Gronberg | A61B 6/032 |
| 2018/0220979 | A1* | 8/2018 | Kojima | A61B 6/542 |
| 2019/0038244 | A1* | 2/2019 | Flohr | A61B 6/06 |
| 2019/0290227 | A1* | 9/2019 | Krauss | A61B 6/032 |
| 2020/0326439 | A1 | 10/2020 | Mccollough et al. | |
| 2021/0405228 | A1 | 12/2021 | Mccollough et al. | |
| 2022/0028127 | A1* | 1/2022 | Daerr | G01T 1/247 |
| 2022/0211338 | A1* | 7/2022 | Kojima | A61B 6/4241 |
| 2023/0255578 | A1* | 8/2023 | Sasaki | A61B 6/032 378/5 |
| 2023/0401768 | A1* | 12/2023 | Li | G06T 12/00 |
| 2024/0374225 | A1* | 11/2024 | Gilat-Schmidt | A61B 6/032 |

FOREIGN PATENT DOCUMENTS

| | | | |
|---|---|---|---|
| JP | 2015-173980 | A | 10/2015 |
| JP | 2016-042934 | A | 4/2016 |
| JP | 2016-055157 | A | 4/2016 |
| JP | 2016-104125 | A | 6/2016 |
| JP | 2019-058488 | A | 4/2019 |
| JP | 6595154 | B2 | 10/2019 |
| JP | 2022-057301 | A | 4/2022 |
| WO | WO 2014/192769 | A1 | 12/2014 |
| WO | WO 2017/073399 | A1 | 5/2017 |

OTHER PUBLICATIONS

Office Action issued Jun. 16, 2026, in corresponding Japanese Patent Application No. 2022-140540, citing documents 1-9 therein, 7 pages.

* cited by examiner

WEIGHT COEFFICIENT

KeV

FIRST RANGE

SECOND RANGE

THIRD RANGE

FOURTH RANGE

WEIGHT COEFFICIENT
KeV
FIRST RANGE
SECOND RANGE
THIRD RANGE
FOURTH RANGE
FIFTH RANGE

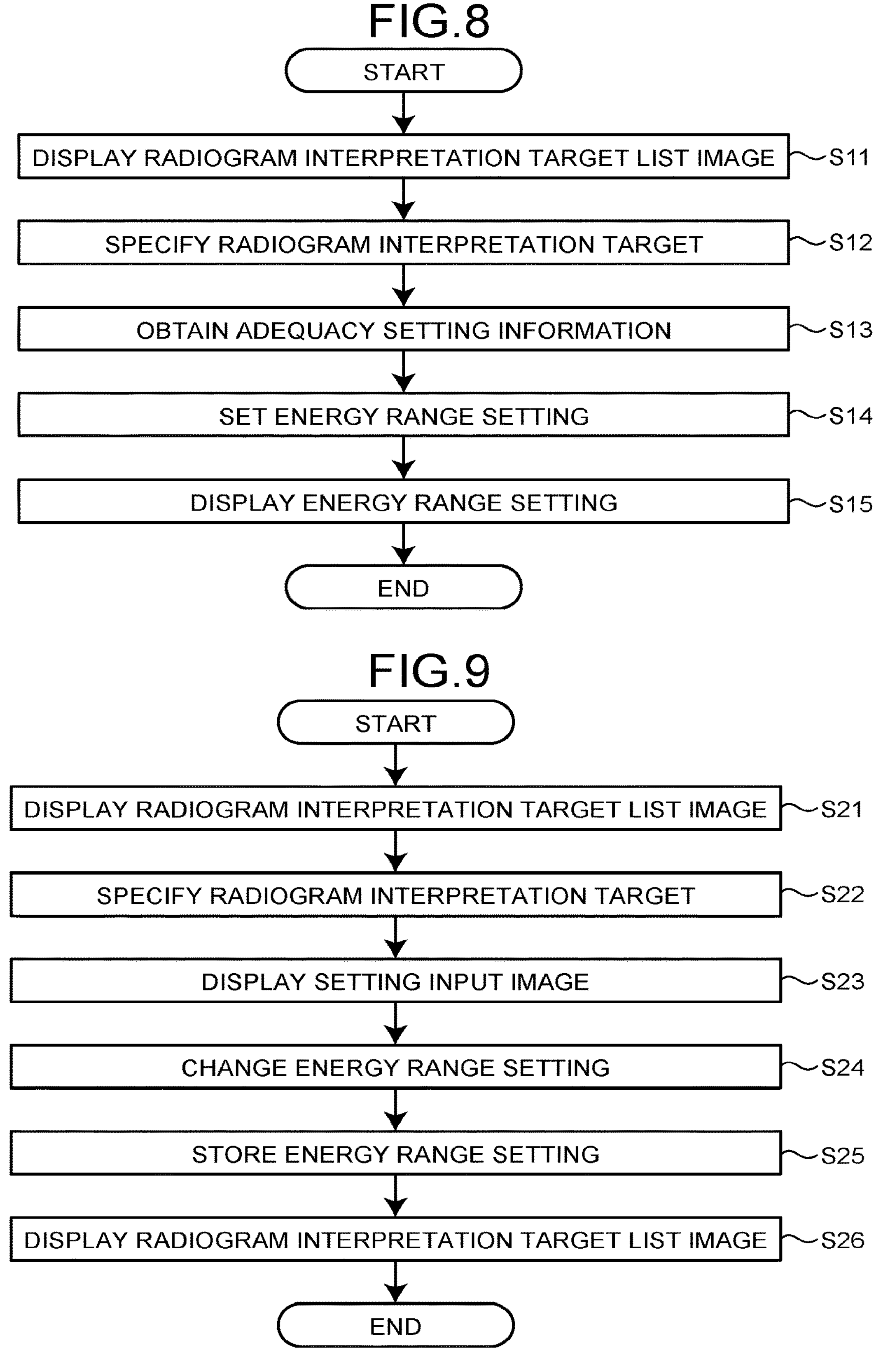
FIG.8
START
DISPLAY RADIOGRAM INTERPRETATION TARGET LIST IMAGE
S11
SPECIFY RADIOGRAM INTERPRETATION TARGET
S12
OBTAIN ADEQUACY SETTING INFORMATION
S13
SET ENERGY RANGE SETTING
S14
DISPLAY ENERGY RANGE SETTING
S15
END
FIG.9
START
DISPLAY RADIOGRAM INTERPRETATION TARGET LIST IMAGE
S21
SPECIFY RADIOGRAM INTERPRETATION TARGET
S22
DISPLAY SETTING INPUT IMAGE
S23
CHANGE ENERGY RANGE SETTING
S24
STORE ENERGY RANGE SETTING
S25
DISPLAY RADIOGRAM INTERPRETATION TARGET LIST IMAGE
S26
END

INFORMATION PROCESSING APPARATUS

CROSS-REFERENCE TO RELATED APPLICATIONS

This application is based upon and claims the benefit of priority from Japanese Patent Application No. 2022-140540, filed on Sep. 5, 2022, the entire contents of which are incorporated herein by reference.

FIELD

Embodiments described herein relate generally to an information processing apparatus.

BACKGROUND

A computed tomography apparatus of the photon counting type (hereinafter, called a photon counting computed tomography (PCCT) apparatus) is capable of performing materials discrimination by counting the number of X-ray photons in each of a plurality of energy ranges.

In such a PCCT apparatus, the volume of data generated by an X-ray detector is tens of times greater as compared to a conventional integral type computed tomography device. Moreover, in a PCCT apparatus, the accuracy of materials discrimination can be enhanced by increasing the number of partitioned energy ranges into a plurality of energy ranges.

However, if the volume of data increases in the process of enhancing the accuracy of materials discrimination, data transfer and data processing becomes a greater burden.

BRIEF DESCRIPTION OF THE DRAWINGS

FIG. 8 is a flowchart for explaining an example of a setting operation performed in the PCCT apparatus according to the first embodiment; and FIG. 9 is a flowchart for explaining an example of an adjustment operation performed in the PCCT apparatus according to the first embodiment.

DETAILED DESCRIPTION

Figure 1:
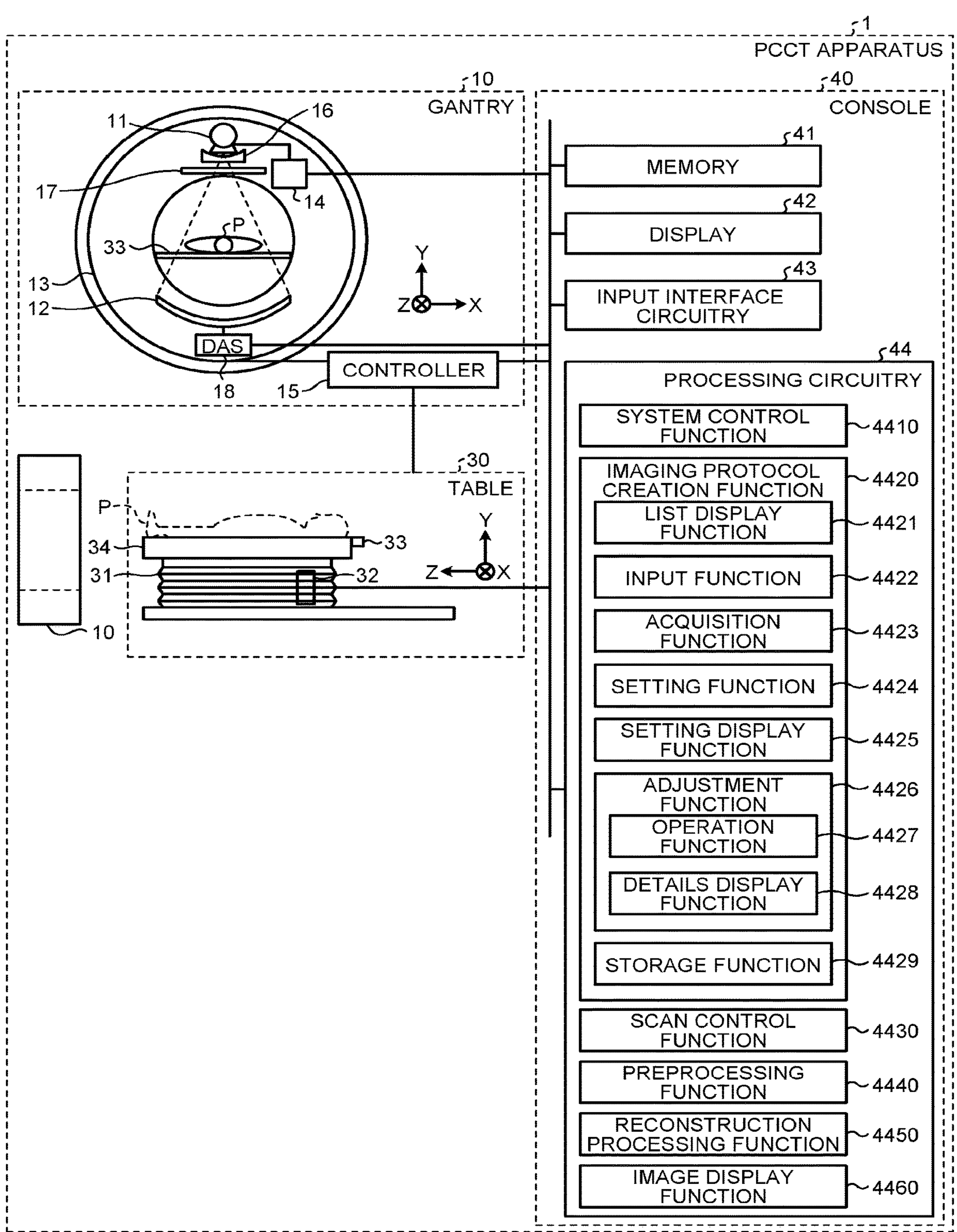
FIG. 1 is a block diagram illustrating an exemplary configuration of a PCCT apparatus according to a first embodiment.

An information processing apparatus according to an embodiment sets an image generation condition for photon counting computed tomography (PCCT) imaging; and includes an input unit, an obtaining unit, and a setting unit. The input unit receives an input that specifies a radiogram interpretation target. Based on target-by-target setting information in which, for each radiogram interpretation target, energy range setting is defined which is related to an energy range meant for discriminating the photons originating from the X-rays that have passed through the subject, the obtaining unit obtains the energy range setting corresponding to the radiogram interpretation target received by the input unit. The setting unit sets the energy range setting as obtained by the obtaining unit.

An exemplary embodiment of an information processing apparatus is described below with reference to the accompanying drawings. In the embodiments described below, the constituent elements having the same reference numerals are assumed to perform identical operations, and their explanation is not given repeatedly.

As an example, the explanation is given for a case in which an information processing apparatus is installed in a photon counting computed tomography (PCCT) apparatus. However, the information processing apparatus is not limited to be integrated with a PCCT apparatus, and alternatively can be installed in some other device.

First Embodiment

FIG. 1 is a block diagram illustrating an exemplary configuration of a PCCT apparatus 1 according to a first embodiment. As illustrated in FIG. 1, the PCCT apparatus 1 includes a gantry 10; a table 30; and a console 40. In the first embodiment, the longitudinal direction of the rotation axis of a rotatable frame 13 in the non-tilted state is defined as the Z-axis direction; the direction that is orthogonal to the Z-axis direction and that is oriented from the center of rotation toward a columnar support meant for supporting the rotatable frame 13 is defined as the X-axis direction; and the direction that is orthogonal to the Z-axis direction and the X-axis direction is defined as the Y-axis direction. Meanwhile, in FIG. 1, a plurality of gantries 10 is illustrated for explanatory convenience. However, in the actual configuration of the PCCT apparatus 1, only a single gantry 10 is present.

The gantry 10 and the table 30 operate either based on an operation performed by an operator using the console 40 or based on an operation performed by an operator using an operating unit provided in the gantry 10 or the table 30. The gantry 10, the table 30, and the console 40 are communicably connected to each other in a wired manner or a wireless manner.

The gantry 10 includes an imaging system that bombards X-rays onto a subject P and collects projection data from the detection data about the X-rays that have passed through the subject P. The gantry 10 includes an X-ray tube 11, an X-ray detector 12, the rotatable frame 13, an X-ray high-voltage generator 14, a controller 15, a wedge 16, a collimator 17, and a data acquisition system (DAS) 18.

The X-ray tube 11 is a vacuum tube that receives the application of a high voltage as well as receives the supply of a filament current from the X-ray high-voltage generator 14, and that generates X-rays by bombarding thermal electrons from a cathode (filament) to an anode (target). When the thermal electrons collide with the target, it results in the generation of X-rays. The X-rays generated at the tube focal position in the X-ray tube 11 pass through an X-ray radiation window formed in the X-ray tube 11; become formed in, for example, a cone-beam shape via the collimator 17; and are bombarded onto the subject P. For example, the X-ray tube 11 can be a rotating anode X-ray tube in which X-rays are generated by bombarding thermal electrons onto a rotating anode.

The X-ray detector 12 detects the photons of the X-rays that are generated in the X-ray tube 11. More particularly, the X-ray detector 12 detects, in units of photons, the X-rays that were bombarded from the X-ray tube 11 and that have passed through the subject P; and outputs, to the DAS 18, an electrical signal corresponding to the X-ray dosage. The X-ray detector 12 includes, for example, a plurality of detection element arrays in each of which a plurality of detection elements (also called X-ray detection elements) is arranged in the fan-angle direction (also called the channel direction) along a single circular arc centered on the focal point of the X-ray tube 11. In the X-ray detector 12, the detection element arrays are flatly arranged along the Z-axis direction. That is, for example, the X-ray detector 12 has a structure in which a plurality of detection element arrays is flatly arranged along the cone-angle direction (also called the row direction or the slice direction).

Meanwhile, the PCCT apparatus 1 can be of various types, such as the rotate/rotate-type (third generation CT) in which the X-ray tube 11 and the X-ray detector 12 rotate as a single unit around the subject P, or the stationary/rotate-type (fourth generation CT) in which a large number of X-ray detection elements arrayed in a ring-like manner are kept fixed and only the X-ray tube 11 rotates around the subject P. Any type of the PCCT apparatus 1 is applicable in the first embodiment.

The X-ray detector 12 is of the direct conversion type and includes a semiconductor device for converting the incident X-rays into an electrical charge. The X-ray detector 12 according to the first embodiment includes, for example, at least a single high-voltage electrode, at least a single semiconductor crystal, and a plurality of read-out electrodes. The semiconductor device is also called an X-ray conversion device. The semiconductor crystal is implemented using, for example, cadmium telluride (CdTe) or cadmium zinc telluride (CdZnTe). In the X-ray detector 12, electrodes are disposed on the two surfaces that are opposite to each other across the semiconductor crystals and that are orthogonal to the Y direction. That is, in the X-ray detector 12, a plurality of anode electrodes (also called read-out electrodes or pixel electrodes) is placed opposite to a cathode electrode (also called a common electrode) across the semiconductor crystals.

In between the read-out electrodes and the common electrodes, a bias voltage is applied. In the X-ray detector 12, when the X-rays get absorbed in the semiconductor crystals, electron-hole pairs are generated and the electrons move toward the anodes (toward the anode electrodes (read-out electrodes)), and the positive holes move toward the cathode (toward the cathode electrode). As a result, a signal related to the detection of the X-rays is output from the X-ray detector 12 to the DAS 18.

Meanwhile, the X-ray detector 12 can also be of the indirect conversion type in which the incident X-rays are converted into electrical signals in an indirect manner. Herein, the X-ray detector 12 represents an example of an X-ray detecting unit.

The rotatable frame 13 is an annular frame that supports the X-ray tube 11 and the X-ray detector 12 opposite to each other and that rotates the X-ray tube 11 and the X-ray detector 12 under the control of the controller 15 (explained later). Meanwhile, in addition to including and supporting the X-ray tube 11 and the X-ray detector 12, the rotatable frame 13 also includes and supports the X-ray high-voltage generator 14 and the DAS 18. The rotatable frame 13 is rotatably supported by the non-rotatable portion of the gantry 10 (for example, by a fixed frame (not illustrated in FIG. 1)). Herein, the rotation mechanism includes, for example, a motor that generates a rotary driving force and a bearing that transmits the rotary driving force to the rotatable frame 13 and causes the rotatable frame 13 to rotate. The motor is disposed in, for example, the non-rotatable portion. The bearing is physically connected to the rotatable frame 13 and the motor, and causes the rotatable frame 13 to rotate according to the torque of the motor. Herein, the rotatable frame 13 represents an example of a rotor.

In the rotatable frame 13 as well as in the non-rotatable portion, communication circuitry is disposed that is either of the contactless type or of the contact type. As a result, the units that are supported by the rotatable frame 13 can communicate with the non-rotatable portion or with external devices of the gantry 10. For example, when optical communication is implemented as the contactless communication method, the detection data generated by the DAS 18 is sent using optical communication from a transmitter, which is disposed in the rotatable frame 13 and which includes a light emitting diode (LED), to a receiver, which includes a photodiode and which is disposed in the non-rotatable portion of the gantry 10. Moreover, the detection data is transferred from the non-rotatable portion to the console 40 using a transmitter. Meanwhile, as the communication method, it is possible to implement contactless data transfer using the capacitive coupling method or the radio wave method, or it is possible to implement a contact-type data transmission method using a slip ring and an electrode brush.

The X-ray high-voltage generator 14 includes electrical circuits such as a transformer and a rectifier. The X-ray high-voltage generator 14 also includes a high-voltage generator having the function of generating a high voltage to be applied onto the X-ray tube 11 and generating a filament current to be supplied to the X-ray tube 11, and includes an X-ray controller for controlling the output voltage according to the X-rays bombarded from the X-ray tube 11. The high-voltage generator can be of the transformer type or the inverter type. Meanwhile, the X-ray high-voltage generator 14 either can be disposed in the rotatable frame 13, or can be disposed in the fixed frame of the gantry 10. The X-ray high-voltage generator 14 represents an example of an X-ray high-voltage generating unit.

The controller 15 includes processing circuitry including a central processing unit (CPU), and includes a driving mechanism including a motor and an actuator. The controller 15 receives an input signal from input interface circuitry 43 (explained later) that is attached to the console 40 or the gantry 10, and accordingly controls the operations of the gantry 10 and the table 30. For example, the controller 15 receives an input signal and performs control to rotate the rotatable frame 13, or performs control to tilt the gantry 10, or performs control to operate the table 30 and a table-top 33. Regarding the control for tilting the gantry 10, according to inclination angle (tilt angle) information input via the input interface attached to the gantry 10, the controller 15 rotates the rotatable frame 13 around the axis parallel to the X-axis direction. Meanwhile, the controller 15 either can be disposed in the gantry 10, or can be disposed in the console 40. The controller 15 represents an example of a control unit.

The wedge 16 is a filter for adjusting the X-ray dosage of the X-rays that are bombarded from the X-ray tube 11. More particularly, the wedge 16 is a filter that transmits and attenuates the X-rays, which are bombarded from the X-ray tube 11, in such a way that the X-rays bombarded from the X-ray tube 11 onto the subject P have a predetermined distribution. For example, the wedge 16 is a wedge filter or a bow-tie filter, and is manufactured by processing aluminum to achieve a predetermined target angle and a predetermined thickness.

The collimator 17 is a lead plate meant for limiting the X-rays, which have passed through the wedge 16, within an X-ray bombardment range, and constitutes a slit because of a combination of a plurality of lead plates. The collimator 17 is sometimes also called an X-ray limiter.

The data acquisition system (DAS) 18 includes a plurality of scaling circuits, each of which includes an amplifier for performing amplification with respect to the electrical signal output from each detection element of the X-ray detector 12, includes an A/D converter for converting the amplified electrical signals into digital signals, and generates detection data representing the result of a counting operation performed using the detection signal obtained the X-ray detector 12. The result of the counting operations represents the data that is assigned with the number of photon of the X-rays in each energy bin. Herein, an energy bin is equivalent to an energy region having a predetermined width. For example, the DAS 18 counts the photons originating from the X-rays that were bombarded from the X-ray tube 11 and that have passed through the subject P (i.e., counts the X-ray photons), and generates, as the detection data, the result of the counting operation in which the energy of the counted photons is discriminated. For example, the DAS 18 generates, as the detection data, the result of counting, for each energy range having the energy range setting as set by a setting function 4424 (explained later), the photons originating from the X-rays that have passed through the subject P. Meanwhile, the DAS 18 represents an example of a data collecting unit.

The detection data generated by the DAS 18 is transferred to the console 40. The detection data represents a set of the following data: the channel number of the detector pixels that generated the detection data; the row number of the detector pixels; the view numbers indicating the collected views (also called the projection angles); and the value indicating the detected X-ray dosage. Meanwhile, as the view angles, it is possible to use the order of collection of the views (the collection timings of the views), or to use the numbers (for example, 1 to 1000) indicating the angles of rotation of the X-ray tube 11. Each of a plurality of counting circuits in the DAS 18 is implemented using a circuit family having circuit elements capable of generating the detection data. In the first embodiment, when simply the term "detection data" is used, it not only includes the meaning of net data that is detected by the X-ray detector 12 and that is not yet subjected to preprocessing, but it also includes the meaning of raw data obtained as a result of performing preprocessing on the net data. Meanwhile, sometimes the data before preprocessing (i.e., the detection data) and the data after preprocessing is collectively referred to as projection data.

The table 30 is an apparatus on which the subject P, who is the target for scanning, is made to lie down and is moved. The table 30 includes a base 31, a table drive circuitry 32, the table-top 33, and a supporting frame 34. The base 31 is a housing that supports the supporting frame 34 to be movable in the vertical direction. The table drive circuitry 32 is a motor or an actuator that moves the table-top 33, on which the subject P is lying down, in the long-axis direction of the table-top 33. The table-top 33 is a plate placed on the upper surface of the supporting frame 34, and the subject P is asked to lie down on the table-top 33. Meanwhile, in addition to moving the table-top 33, the table drive circuitry 32 can also drive the supporting frame 34 in the long-axis direction of the table-top 33.

The console 40 includes a memory 41, a display 42, an input interface circuitry 43, and a processing circuitry 44. Among the memory 41, the display 42, the input interface circuitry 43, and the processing circuitry 44; the data communication is performed, for example, via a bus. Herein, the console 40 is a separate apparatus from the gantry 10. However, alternatively, either the entire console 40 or some of its constituent elements can be included in the gantry 10.

The memory 41 is implemented, for example, using a semiconductor memory device such as a random access memory (RAM) or a flash memory, or using a hard disk drive (HDD) or a solid state drive (SSD), or using an optical disc. Alternatively, the memory 41 can be a driving device that performs reading and writing of information either with respect to a portable memory medium such as a compact disc (CD), a digital versatile disc (DVD), or a flash memory, or with respect to a semiconductor device such as a random access memory (RAM).

The memory 41 is used to store, for example, the detection data output from the DAS 18, the projection data generated by a preprocessing function 4440, and reconstructed images obtained by a reconstruction processing function 4450. A reconstructed image represents, for example, three-dimensional CT image data (volume data) or two-dimensional CT image data. Moreover, the storage area of the memory 41 can be provided inside the PCCT apparatus 1 or inside an external storage apparatus connected by a network.

The memory 41 is also used to store target-by-target setting information. In the target-by-target setting information, for each radiogram interpretation target, energy range setting is defined that is related to the energy ranges meant for discriminating the photons originating from the X-rays which have passed through the subject P. That is, in the target-by-target setting information, radiogram interpretation target information and adequacy setting information are held in a corresponding manner.

The radiogram interpretation information indicates a radiogram interpretation target about which a healthcare personnel performs radiogram interpretation. In other words, in CT image data, the radiogram interpretation target represents the target for highlighted display. Herein, the highlighted display implies a display that enables discrimination. For example, the body tissues constituting the subject P, such as the fat, the muscles, the skin, the bones, the nervous system, the blood vessels, or the internal organs, represent the radiogram interpretation target. Alternatively, the radiogram interpretation target can be materials constituting the subject P, such as water, calcium, and iodine. Meanwhile, a single set of radiogram interpretation target information is not limited to contain a single radiogram interpretation target and alternatively can contain a plurality of radiogram interpretation targets. For example, the radiogram interpretation target information can contain a combination of one or more body tissues and one or more materials.

Moreover, the radiogram target information can also contain a plurality of radiogram interpretation targets that cannot be individually highlighted. That is, consider a case in which, when a radiogram interpretation target A is highlighted, a radiogram interpretation target B inevitably gets highlighted; the radiogram interpretation target information can contain both the radiogram interpretation targets A and B.

Figure 2:
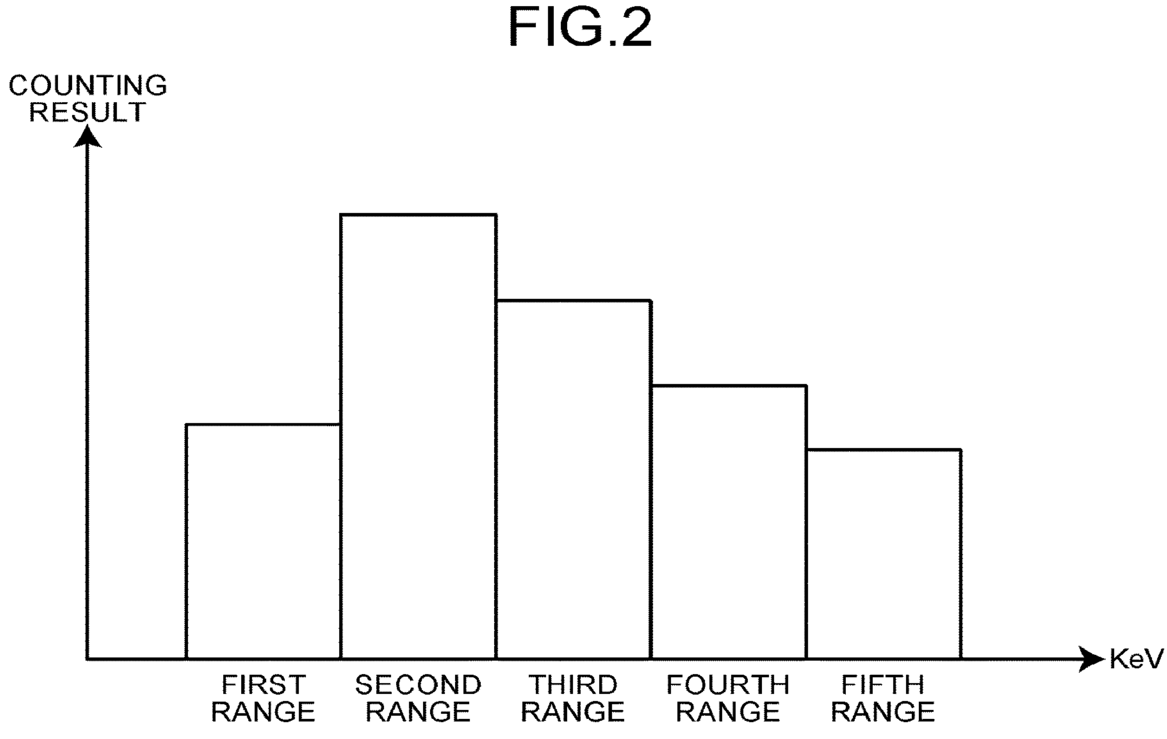
FIG. 2 is a diagram illustrating an example of a counting result obtained by performing discrimination for each energy range.

The adequacy setting information indicates the setting appropriate for the radiogram interpretation target that is indicated by the radiogram interpretation target information corresponding to the adequacy setting information, and represents the setting about a plurality of energy ranges meant for discriminating the photons originating from the X-rays that have passed through the subject P. FIG. 2 is a diagram illustrating an example of the counting result obtained by performing discrimination for each energy range. As illustrated in FIG. 2, for each energy range, the PCCT apparatus 1 counts the photons originating from the X-rays that have passed through the subject P. In FIG. 2 is illustrated an example in which the photons are counted for each of five energy ranges, namely, a first range, a second range, a third range, a fourth range, and a fifth range.

For example, the adequacy setting information indicates the number of energy ranges, the width of each energy range, and the weight coefficient of each energy range. The number of energy ranges indicates the number of partitioned energy ranges. The width of each energy range indicates the upper limit value and the lower limit value of that energy range. The weight coefficient is set with respect to the counting result in each energy range. The weight coefficient is set in order to vary the influence rate of the corresponding counting result on the CT image data. That is, a higher weight coefficient indicates a large counting result, and a lower weight coefficient indicates a small counting result.

Meanwhile, the target-by-target setting information is not limited to be stored in the memory 41, and alternatively can be stored in the memory medium of some other apparatus. Moreover, the radiogram interpretation target information and the adequacy setting information are not limited to be treated as a single set of target-by-target setting information, and can be partitioned into a plurality of sets of information.

The display 42 is used to display a variety of information. For example, the display 42 outputs a medical image (a CT image) generated by the processing circuitry 44 or outputs a graphical user interface (GUI) meant for receiving a variety of operations from the operator. As the display 42, for example, a liquid crystal display (LCD), a cathode ray tube (CRT) display, an organic electro luminescence display (OLED), a plasma display, or some other arbitrary type of display can be used. Meanwhile, the display 42 can alternatively be disposed in the gantry 10. The display 42 either can be of the desktop type or can be configured with a tablet terminal capable of performing wireless communication with the main body of the console 40. Herein, the display 42 represents an example of a display unit.

The input interface circuitry 43 receives various input operations from the operator, converts the input operations into electrical signals, and outputs the electrical signals to the processing circuitry 44. For example, from the operator, the input interface circuitry 43 receives a collection condition to be implemented at the time of collecting the projection data, or receives a reconstruction condition to be implemented at the time of reconstructing the CT image data, or receives an image processing condition related to the postprocessing to be performed with respect to the CT image data. The postprocessing can be performed either in the console 40 or in an external workstation. Alternatively, the postprocessing can be performed in the console 40 and a workstation at the same time. The postprocessing as defined herein represents the concept of pointing out the processing to be performed with respect to an image reconstructed by the reconstruction processing function 4450. For example, the postprocessing includes multi planar reconstruction (MPR) display of reconstructed images or includes rendering of volume data. Meanwhile, as the input interface circuitry 43, it is possible to use, for example, a mouse, a keyboard, a trackball, switches, buttons, a joystick, a touch-pad, or a touch-sensitive panel.

However, in the first embodiment, the input interface circuitry 43 is not limited to include a physical operating component such as a mouse, a keyboard, a trackball, switches, buttons, a joystick, a touchpad, or a touch-sensitive panel. Alternatively, for example, the input interface circuitry 43 can be an electric-signal processing circuit that, from an independently-installed external input device, receives an electric signal corresponding to an input operation, and outputs that electric signal to the processing circuitry 44. The input interface circuitry 43 represents an example of an input unit. Meanwhile, the input interface circuitry 43 can alternatively be installed in the gantry 10. Moreover, the input interface circuitry 43 can be configured with a tablet terminal capable of performing wireless communication with the main body of the console 40.

The processing circuitry 44 controls the operations of the entire PCCT apparatus 1. For example, the processing circuitry 44 includes a system control function 4410, an imaging protocol creation function 4420, a list display function 4421, an input function 4422, an acquisition function 4423, the setting function 4424, a setting display function 4425, an adjustment function 4426, an operation function 4427, a details display function 4428, a storage function 4429, a scan control function 4430, the preprocessing function 4440, the reconstruction processing function 4450, and an image display function 4460. In the first embodiment, the processing functions implemented in the system control function 4410, the imaging protocol creation function 4420, the list display function 4421, the input function 4422, the acquisition function 4423, the setting function 4424, the setting display function 4425, the adjustment function 4426, the operation function 4427, the details display function 4428, the storage function 4429, the scan control function 4430, the preprocessing function 4440, the reconstruction processing function 4450, and the image display function 4460, which represent the constituent elements, are stored as computer-executable programs in the memory 41. The processing circuitry 44 is a processor that reads the computer programs from the memory 41 and executes them, so that the function corresponding to each computer program gets implemented. In other words, after having read the computer programs, the processing circuitry 44 gets equipped with the functions illustrated in the processing circuitry 44 in FIG. 1.

With reference to FIG. 1, it is explained that the system control function 4410, the imaging protocol creation function 4420, the list display function 4421, the input function 4422, the acquisition function 4423, the setting function 4424, the setting display function 4425, the adjustment function 4426, the operation function 4427, the details display function 4428, the storage function 4429, the scan control function 4430, the preprocessing function 4440, the reconstruction processing function 4450, and the image display function 4460 are implemented in a single processor. However, alternatively, the processing circuitry 44 can be configured by combining a plurality of independent processors, and each processor can be made to execute computer programs and implement the corresponding functions. Moreover, with reference to FIG. 1, it is explained that the computer programs corresponding to the processing functions are stored in a single memory circuit such as the memory 41. Alternatively, a plurality of memory circuits can be disposed in a dispersed manner, and the processing circuitry 44 can be configured to read the computer programs from the corresponding memory circuits.

In the explanation given above, the term "processor" implies a circuit such as a central processing unit (CPU), or a graphical processing unit (GPU), or an application specific integrated circuit (ASIC), or a programmable logic device (for example, a simple programmable logic device (SPLD), a complex programmable logic device (CPLD), or a field programmable gate array (FPGA)). A processor reads computer programs stored in the memory 41, executes them, and implements the corresponding functions. Meanwhile, instead of storing the computer programs in the memory 41, they can be directly incorporated in the circuit of the processor. In that case, the processor reads the computer programs incorporated in the circuit thereof, executes them, and implements the corresponding functions.

As illustrated in FIG. 2, the PCCT apparatus 1 counts, for each energy range, the photons originating from the X-rays that have passed through the subject P. The PCCT apparatus 1 can segmentalize the energy range and, as the number of partitioned energy ranges increases, can generate CT image data enabling discrimination of various materials. However, as a result of segmentalizing the energy range and increasing its number of divisions, the X-ray detector 12 outputs a greater number of sets of data. For that reason, as a result of segmentalizing the energy range and increasing its number of divisions, data transfer and data processing becomes a greater burden.

There are times when the purpose of examination using the PCCT apparatus 1 is already decided, that is, the radiogram interpretation target is already decided. If the radiogram interpretation target is already decided, then the processing circuitry 44 sets the energy ranges appropriate for that radiogram interpretation target, so that an increase in the volume of data can be held down while maintaining the accuracy of materials discrimination in the radiogram interpretation target. In other words, the PCCT apparatus 1 enables achieving reduction in the volume of data as compared to the case in which the energy range is segmentalized beyond necessity and its number of divisions is increased.

In that regard, the processing circuitry 44 sets image generation conditions for PCCT imaging. Thus, the processing circuitry 44 sets image generation conditions regarding the imaging of the subject P as performed by the PCCT apparatus 1. The image generation conditions represent various conditions set up to the generation of CT image data. Examples of the image generation conditions include a scanning condition regarding scanning of the subject P, a reconstruction condition regarding reconstruction with respect to the projection data obtained by scanning, and an image processing condition indicating the condition for image processing such as preprocessing to be performed before reconstruction or postprocessing to be performed after reconstruction. The image generation conditions include the number of partitioned energy ranges meant for discriminating the photons originating from the X-rays that have passed through the subject P, includes the width of each energy range, and includes the weight coefficient of each energy range.

More specifically, the processing circuitry 44 has the following various functions.

The system control function 4410 controls the functions of the processing circuitry 44 based on an input operation received from the operator via the input interface circuitry 43. Moreover, the system control function 4410 reads a control program stored in the memory 41, loads it in the memory of the processing circuitry 44, and controls the constituent elements of the PCCT apparatus 1 according to the control program.

The imaging protocol creation function 4420 creates an imaging protocol to be used in taking images of the subject P. The imaging protocol represents information in which a sequence of operations and various settings are defined in regard to scanning the subject P, performing reconstruction with respect to the projection data obtained by scanning, and displaying CT image data generated as a result of reconstruction. More specifically, the imaging protocol includes the body part of the subject P that is to be scanned, includes a scanning condition to be implemented at the time of scanning the subject P, a collection condition to be implemented at the time of collecting projection data, and a reconstruction condition to be implemented at the time of performing reconstruction with respect to the projection data.

Moreover, the imaging protocol includes the setting related to the energy ranges meant for discriminating the photons originating from the X-rays that have passed through the subject P, and includes the setting about the radiogram interpretation target. That is, while creating the imaging protocol, the imaging protocol creation function 4420 receives the setting related to the energy ranges and the setting about the radiogram interpretation target.

More specifically, the imaging protocol creation function 4420 includes a list display function 4421, an input function 4422, an acquisition function 4423, a setting function 4424, a setting display function 4425, an adjustment function 4426, and a storage function 4429.

The list display function 4421 displays, based on the target-by-target setting information, a radiogram interpretation target list image that includes a list of the radiogram interpretation targets. The list display function 4421 represents an example of a list displaying unit. In a radiogram interpretation target list image, radiogram interpretation targets that are indicated by the radiogram interpretation target information of the target-by-target setting information are listed in a selectable manner. The user selects a radiogram interpretation target, which represents the selected target for highlighted display.

Consider a case in which, when a first radiogram interpretation target is highlighted from among the radiogram interpretation targets listed in the radiogram interpretation target list image, a second radiogram interpretation target also gets highlighted. In that case, the list display function 4421 displays the first radiogram interpretation target and the second radiogram interpretation target as a single selection option. That is, when a plurality of radiogram interpretation targets that cannot be highlighted individually is included in the radiogram interpretation target information of the target-by-target setting information, the list display function 4421 displays those radiogram interpretation targets as a single selection option. Meanwhile, for example, the list display function 4421 can display a plurality of radiogram interpretation targets, which is included in the radiogram interpretation target information, side-by-side; or can display generic terms for a plurality of radiogram interpretation targets included in the radiogram interpretation target information; or can display representative radiogram interpretation targets from among a plurality of radiogram interpretation targets included in the radiogram interpretation target information; or can display the radiogram interpretation targets according to some other method.

Moreover, the list display function 4421 can display, in a radiogram interpretation target list image, the overview of the energy range setting in a corresponding manner to the radiogram interpretation targets. For example, the list display function 4421 can display the number of partitioned energy ranges, the width of each energy range, and the weight coefficient of each energy range.

The input function 4422 receives an input that specifies a radiogram interpretation target. The input function 4422 represents an example of an input unit. For example, the input function 4422 receives the specification of one or more radiogram interpretation targets from the radiogram interpretation target list image displayed by the list display function 4421. Meanwhile, an operation of selecting a radiogram interpretation target is not the only possible case of specifying a radiogram interpretation target. Alternatively, as a result of an operation performed to input a character string or numerical digits indicating a radiogram interpretation target, the input function 4422 can receive an input that specifies the radiogram interpretation target. Still alternatively, according to some other method, the input function 4422 can receive an input that specifies the radiogram interpretation target.

Based on the target-by-target setting information in which the energy range setting, which is related to the energy ranges meant for discriminating the photons originating from the X-rays that have passed through the subject P, is defined for each radiogram interpretation target; the acquisition function 4423 obtains the energy range setting corresponding to the radiogram interpretation target received by the input function 4422. That is, based on the target-by-target setting information in which the radiogram interpretation target information is associated to the adequacy setting information related to the energy ranges meant for discriminating the photons originating from the X-rays that have passed through the subject P, the acquisition function 4423 obtains the adequacy setting information associated to the radiogram interpretation target information that indicates the radiogram interpretation target received by the input function 4422. The acquisition function 4423 represents an example of an obtaining unit. Meanwhile, if a plurality of radiogram interpretation targets is selected and is received by the input function 4422, then the acquisition function 4423 obtains the adequacy setting information associated to each of the selected radiogram interpretation targets.

The setting function 4424 sets the energy range setting for the adequacy setting information obtained by the acquisition function 4423. The setting function 4424 represents an example of a setting unit. The energy range setting implies the setting for defining each energy range from among the energy ranges meant for discriminating the photons originating from the X-rays that have passed through the subject P. In the energy range setting, the setting function 4424 sets the number of partitioned energy ranges, the width of each energy range, and the weight coefficient of the energy range.

More specifically, when a plurality of radiogram interpretation targets is selected and is received by the input function 4422 and when the adequacy setting information corresponding to each radiogram interpretation target is obtained, the setting function 4424 sets the energy range setting for each set of adequacy setting information. Meanwhile, in case setting the energy range setting for each set of adequacy setting information results in a competition among the energy range settings, the setting function 4424 can set the energy range setting of those sets of adequacy setting information which are identified according to a preset order of priority, or can set an intermediate value of the energy range setting for each set of adequacy setting information.

The setting display function 4425 displays at least some part of the energy range setting that is set by the setting function 4424. The setting display function 4425 represents an example of a setting display unit. Thus, the setting display function 4425 displays, from the energy range setting, at least either the number of partitioned energy ranges, or the width of each energy range, or the weight coefficient of each energy range. With that, the setting display function 4425 notifies the type of setting according to which the subject P would be scanned.

The adjustment function 4426 adjusts, in the adequacy setting information or the target-by-target setting information, the energy range setting for each radiogram interpretation target. The adjustment function 4426 represents an example of an adjusting unit. For example, for each radiogram interpretation target, the adjustment function 4426 adjusts the number of partitioned energy ranges. Moreover, the adjustment function 4426 adjusts the weight coefficient of each energy range of each radiogram interpretation target. More specifically, the adjustment function 4426 includes the operation function 4427 and the details display function 4428.

The operation function 4427 receives an operation of selecting, from the radiogram interpretation targets listed in the radiogram interpretation target list image, a radiogram interpretation target for which the energy range setting is to be adjusted. The details display function 4428 displays a setting input image to be used in adjusting the energy range setting of the adequacy setting information corresponding to the selected radiogram interpretation target. Meanwhile, if there is no appropriate radiogram interpretation target among the radiogram interpretation targets listed in the radiogram interpretation target list image, then the operation function 4427 can receive an operation of newly creating a combination of the radiogram interpretation target information and the adequacy setting information.

Moreover, in the energy range setting of each radiogram interpretation target, the details display function 4428 displays at least either the number of partitioned energy ranges or the weight coefficient of each energy range. The details display function 4428 represents an example of a details displaying unit. The operation function 4427 receives, via the setting input image, an operation of changing the energy range setting. Thus, the setting input image represents a graphical user interface (GUI) meant for receiving an operation of changing the energy range setting. For example, the operation function 4427 receives an operation of changing at least either the number of partitioned energy ranges or the weight coefficient of each energy range as displayed by the details display function 4428. Meanwhile, the operation function 4427 represents an example of an operating unit.

Figure 3:
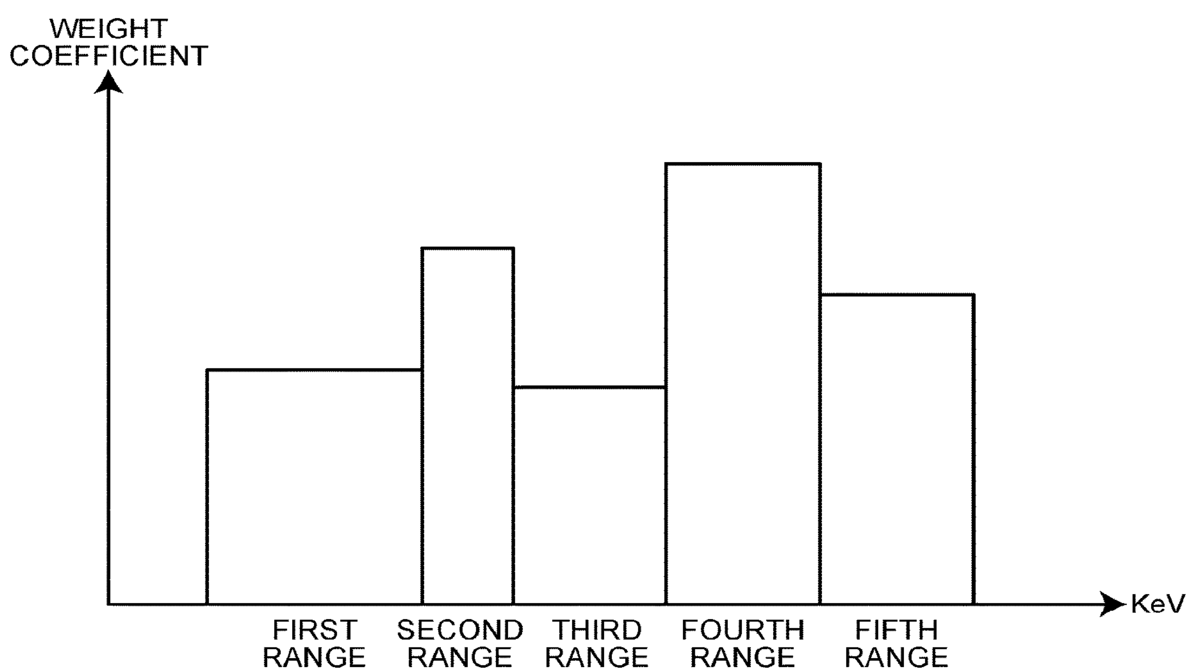
FIG. 3 is a diagram illustrating an example of a setting input image in the case in which the widths of energy ranges are changed.

For example, the details display function 4428 displays the setting input image via which an input for changing the width of each energy range is received. FIG. 3 is a diagram illustrating an example of the setting input image in the case in which the widths of the energy ranges are changed. Thus, the specification of the energy ranges and the specification of the weight coefficient of each energy range is received via the setting input image. Herein, the horizontal axis represents the energy ranges. Thus, on the horizontal axis, a plurality of energy ranges is set for discriminating the photons originating from the X-rays that have passed through the subject P. In the setting input image illustrated in FIG. 3, five energy ranges, namely, a first range, a second range, a third range, a fourth range, and a fifth range are set. The vertical axis represents the weight coefficient of each energy range. In the setting input image illustrated in FIG.

3, the weight coefficient is set for each of the five energy ranges, namely, the first range, the second range, the third range, the fourth range, and the fifth range.

The operation function 4427 receives, via the setting input image, an input for changing the widths of the energy ranges. More specifically, when any energy ranges are selected from among a plurality of energy ranges, the operation function 4427 receives an input that specifies the upper limit values or the lower limit values of the selected energy ranges. In the setting input image illustrated in FIG. 3, the first range is expanded in width and the second range is narrowed in width.

Figures 4, 5:
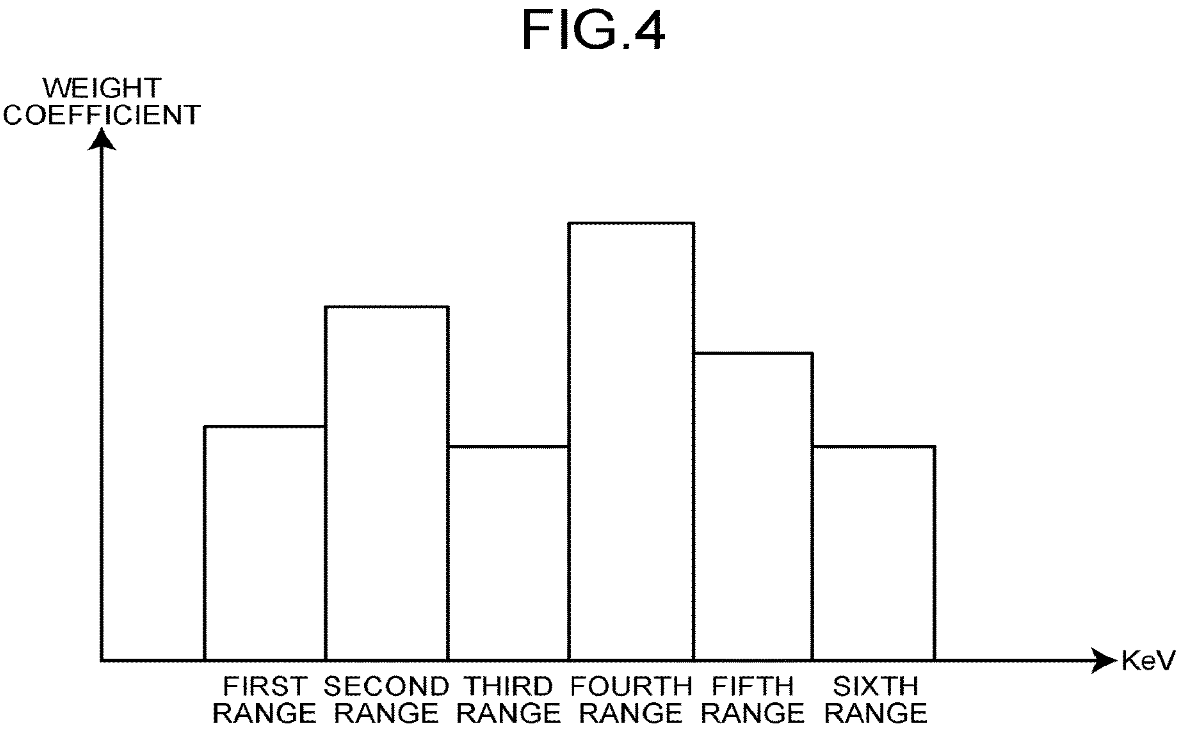
FIG. 4 is a diagram illustrating an example of a setting input image in the case in which the number of partitions energy ranges is increased.
FIG. 5 is a diagram illustrating an example of a setting input image in the case in which the number of partitions energy ranges is reduced.

For example, the details display function 4428 displays a setting input image meant for receiving an input for increasing the number of partitioned energy ranges. FIG. 4 is a diagram illustrating an example of the setting input image in the case in which the number of partitions energy ranges is increased. In the setting input image illustrated in FIG. 4, six energy ranges, namely, a first range, a second range, a third range, a fourth range, a fifth range, and a sixth range are set. That is, in the setting input image illustrated in FIG. 4, the number of energy ranges has increased by one.

The operation function 4427 receives, via the setting input image, an input for increasing the number of partitioned energy ranges. More specifically, when there is an addition of an energy range, the operation function 4427 receives an operation of specifying whether to treat, as the target energy ranges, the same number of energy ranges before the addition or whether to add such an energy range which was not treated as a target energy range before the addition. For example, if there are five energy ranges before the addition and if the number of energy ranges becomes six after the addition, then the operation function 4427 receives an operation of specifying whether to partition the range, which was partitioned into fifths with five energy ranges, is to be partitioned into sixth with six energy ranges and whether to treat the new energy range as the sixth range.

If the same number of energy ranges before the addition are to be treated as the target energy ranges, then the operation function 4427 either can receive an operation of narrowing the width of each energy range or can receive an operation of narrowing the width of the selected energy ranges. Alternatively, if a new energy range is to be treated as a target energy range, then the operation function 4427 receives an operation of specifying whether to treat an energy range on the side of lower energy or an energy range on the side of higher energy as a target energy range.

For example, the details display function 4428 displays the setting input image meant for receiving an input for reducing the number of partitioned energy ranges. FIG. 5 is a diagram illustrating an example of the setting input image in the case in which the number of partitions energy ranges is reduced. In the setting input image illustrated in FIG. 5, four energy ranges, namely, a first range, a second range, a third range, and a fourth range are set. That is, in the setting input image illustrated in FIG. 5, one energy range has been deleted.

Moreover, the operation function 4427 receives, via the setting input image, an input for reducing the number of partitioned energy ranges. More specifically, when any energy range is deleted, the operation function 4427 receives an operation of specifying the manner of dealing with the deleted energy range. For example, if there are five energy ranges before the deletion and if the number of energy ranges becomes four after the deletion, then the operation function 4427 receives an operation of specifying whether to partition the range, which was partitioned into fifths with five energy ranges, is to be partitioned into quarters with four energy ranges and whether to narrow any of the energy ranges.

Figures 6, 7:
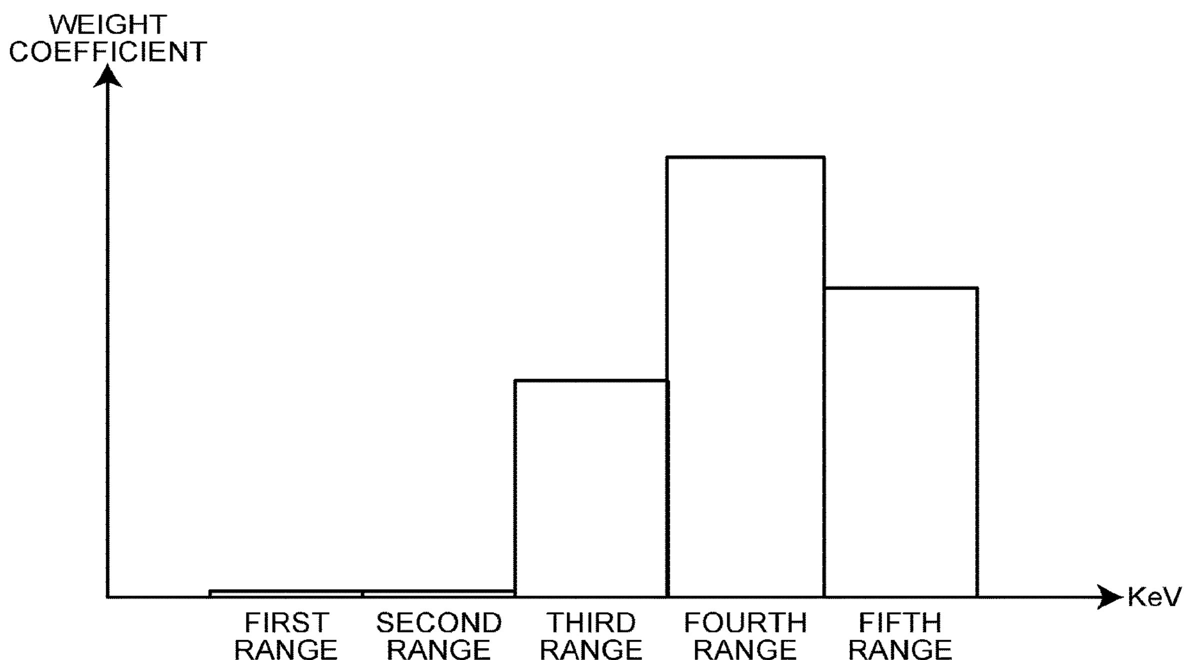
FIG. 6 is a diagram illustrating an example of a setting input image in the case in which the weight coefficients of the energy ranges are changed.
FIG. 7 is a diagram illustrating an example of a setting input image in the case in which the weight coefficients of the energy ranges are changed to zero.

For example, the details display function 4428 displays the setting input image meant for receiving an input for changing the weight coefficients of the energy ranges. FIG. 6 is a diagram illustrating an example of the setting input image in the case in which the weight coefficients of the energy ranges are changed. The operation function 4427 receives, via the setting input image, an input for changing the weight coefficients of the energy ranges. That is, the operation function 4427 receives an input that specifies whether to increase or reduce the weight coefficient of each energy range. In the setting input image illustrated in FIG. 6, the weight coefficient of the first range is reduced, and the weight coefficients of the fourth and fifth ranges are increased.

Moreover, the operation function 4427 receives, via the setting input image, an input for reducing the weight coefficients of particular energy ranges to zero. FIG. 7 is a diagram illustrating an example of the setting input image in the case in which the weight coefficients of some energy ranges are changed to zero. In the setting input image illustrated in FIG. 7, the weight coefficients of the first and second ranges are set to zero.

The storage function 4429 stores the energy range setting that corresponds to the radiogram interpretation targets and that is adjusted by the adjustment function 4426. The storage function 4429 represents an example of a storing unit. More specifically, the storage function 4429 stores the energy range setting that is specified by an operation received by the operation function 4427 via the setting input image which is displayed by the details display function 4428.

The storage function 4429 either can store the concerned energy range setting by overwriting the existing energy range setting, or can store the concerned energy range setting as separate energy range setting. When the operation function 4427 receives an operation of specifying the overwrite save, the storage function 4429 accordingly updates the adequacy setting information. That is, the storage function 4429 updates the adequacy setting information to the energy range setting specified in the operation that is received by the operation function 4427 via the setting input image.

Alternatively, if the operation function 4427 receives an operation of specifying to store the concerned energy range setting as separate energy range setting, then the storage function 4429 stores the radiogram interpretation target of the radiogram target information corresponding to the concerned adequacy setting information as separate energy rang setting. Then, the storage function 4429 adds, in the target-by-target setting information, the adequacy setting information of the energy range setting, which is specified in the operation received by the operation function 4427 via the setting input image, in a corresponding manner to the radiogram interpretation target information indicating the specified radiogram interpretation target. Moreover, when such an addition is performed by the storage function 4429, the list display function 4421 displays a radiogram interpretation target list image that includes the energy range setting stored by the storage function 4429 as well as the already-stored energy range setting.

The operation function 4427 can receive an operation of displaying a sample image in the case in which CT scanning is performed according to the energy range setting of the adequacy setting information. When the operation function 4427 receives an operation of displaying a sample image, the details display function 4428 displays, as the sample image, the CT image data that has been obtained as a result of the CT scanning performed by the scan control function 4430 and that has been subjected to reconstruction by the reconstruction processing function 4450. For example, the details display function 4428 displays a setting input image in which the sample image is included.

Meanwhile, there are times when the operation function 4427 does not receive an operation of changing the number of partitioned energy ranges or changing the width of each energy range, but receives an operation of changing the weight coefficient of each energy range. Thus, the storage function 4429 happens to store the change in the weight coefficient of each energy range. In that case, according to the energy range setting of each set of adequacy setting information in which the weight coefficient of an energy range has been changed, the reconstruction processing function 4450 performs reconstruction processing with respect to the existing projection data obtained by scanning the subject P. The reconstruction processing function 4450 represents an example of a reconstructing unit. That is, the reconstruction processing function 4450 performs reconstruction processing with respect to the projection data stored in the picture archiving and communication system (PACS) or in the memory 41. Then, the details display function 4428 displays CT image data that is generated as a result of performing reconstruction according to the weight coefficient of each energy range. The details display function 4428 represents an example of an image display unit. For example, the details display function 4428 displays the generated CT image data as the sample image. For example, the details display function 4428 displays a setting input image in which the sample image is included.

The scan control function 4430 controls the CT scanning performed in the gantry 10. That is, the scan control function 4430 controls the CT scanning of the subject P performed according to the energy range setting that is set by the setting function 4424.

The preprocessing function 4440 generates projection data as a result performing preprocessing such as logarithmic conversion or offset correction, inter-channel sensitivity correction, and beam hardening correction with respect to the detection data output from the DAS 18.

The reconstruction processing function 4450 performs reconstruction processing with respect to the projection data, which is generated by the preprocessing function 4440, using the filtered back projection (FBP) method; and generates CT image data. The reconstruction includes various operations including various correction operations, such as scattering correction and beam hardening correction, and including application of a reconstruction function in the reconstruction condition. Moreover, the reconstruction processing function 4450 performs reconstruction processing according to the weight coefficient of each energy range set by the setting function 4424. As a result, the reconstruction processing function 4450 generates CT image data according to the weight coefficient of each energy range set by the setting function 4424.

Furthermore, when one or more radiogram interpretation targets are selected and are received by the input function 4422, the reconstruction processing function 4450 performs reconstruction processing based on the adequacy setting information corresponding to each selected radiogram interpretation target. That is, the reconstruction processing function 4450 performs reconstruction processing of each energy range, which is set in the corresponding adequacy setting information, according to the weight coefficient set in that adequacy setting information. As a result, the reconstruction processing function 4450 generates CT image data that enables discrimination of a plurality of radiogram interpretation targets using the input function 4422. Meanwhile, when a plurality of radiogram interpretation targets are selected and are received by the input function 4422, the image display function 4460 can generate, for each selected radiogram interpretation target, CT image data in which that radiogram interpretation target is highlighted.

Meanwhile, the reconstruction processing performed by the reconstruction processing function 4450 is not limited to the FBP method, and alternatively it is possible to implement other known methods such as implementing the successive approximation reconstruction method or using a deep neural network that outputs a reconstructed image in response to the input of projection data. The reconstruction processing function 4450 stores the reconstructed CT image data in the memory 41. Meanwhile, the reconstruction processing performed by the reconstruction processing function 4450 is not limited to generating an image based on pre-reconstruction data such as projection data, and implies reconstruction processing in a broad sense.

The image display function 4460 displays CT image data, which is generated when the reconstruction processing function 4450 performs reconstruction processing based on the adequacy setting information corresponding to the radiogram interpretation target that is selected and is received by the input function 4422. As a result, when a plurality of radiogram interpretation targets is selected and is received by the input function 4422, the image display function 4460 can display CT image data in which the selected radiogram interpretation targets are highlighted. That is, the image display function 4460 displays CT image data that enables discrimination of the radiogram interpretation targets that are selected and are received by the input function 4422. Moreover, if CT image data is generated for each of a plurality of radiogram interpretation targets that are selected and are received by the input function 4422, the image display function 4460 can display each set of CT image data.

Given below is the explanation of the setting operation performed in the PCCT apparatus 1. The setting operation is performed to set the energy range setting according to the radiogram interpretation target.

FIG. 8 is a flowchart for explaining an example of the setting operation performed in the PCCT apparatus 1 according to the first embodiment.

The list display function 4421 displays, based on the target-by-target setting information, a radiogram interpretation target list image in which the radiogram interpretation targets are listed (Step S11).

The input function 4422 receives an operation of specifying a radiogram interpretation target from among the radiogram interpretation targets listed in the radiogram interpretation target list image (Step S12).

The acquisition function 4423 obtains the adequacy setting information corresponding to the radiogram interpretation target information indicating the specified radiogram interpretation target (Step S13).

The setting function 4424 sets the energy range setting that is indicated by the obtained adequacy setting information (Step S14).

The setting display function 4425 displays at least some part of the energy range setting (Step S15). For example, the setting display function 4425 displays the number of partitioned energy ranges, or the width of each energy range, or the weight coefficient of each energy range.

With that, the PCCT apparatus 1 ends the setting operation.

Given below is the explanation of the adjustment operation performed by the PCCT apparatus 1. The adjustment operation is performed to adjust the energy range setting according to the radiogram interpretation target.

FIG. 9 is a flowchart for explaining an example of the adjustment operation performed in the PCCT apparatus 1 according to the first embodiment.

The list display function 4421 displays, based on the target-by-target setting information, a radiogram interpretation target list image in which the radiogram interpretation targets are listed (Step S21).

The operation function 4427 receives an operation of specifying the radiogram interpretation target from among the radiogram interpretation targets listed in the radiogram interpretation target list image (Step S22).

The details display function 4428 displays a setting input image meant for adjusting the energy range setting of the adequacy setting information corresponding to the selected radiogram interpretation target (Step S23).

The operation function 4427 receives, via the setting input image, an operation of changing the energy range setting (Step S24).

When the operation function 4427 receives an operation of storing the energy range setting, the storage function 4429 adds the changed energy range setting to the target-by-target setting information (Step S25). That is, the storage function 4429 adds, to the target-by-target setting information, the combination of the adequacy setting information corresponding to the changed energy range setting and the radiogram interpretation target information.

The list display function 4421 displays, based on the target-by-target setting information, a radiogram interpretation target list image in which radiogram interpretation targets including the added radiogram interpretation target are listed (Step S26).

With that, the PCCT apparatus 1 ends the adjustment operation.

As explained above, in the PCCT apparatus 1 according to the first embodiment, an input that specifies the radiogram interpretation target is received. Moreover, in the PCCT apparatus 1, based on the target-by-target setting information in which, for each radiogram interpretation target, the energy range setting is defined that is related to the energy ranges meant for discriminating the photons originating from the X-rays that have passed through the subject P; the energy range setting corresponding to the specified radiogram interpretation target is obtained. Then, in the PCCT apparatus 1, the obtained energy range setting is set. With that, the PCCT apparatus 1 scans the subject P according to the setting that is appropriate for the specified radiogram interpretation target. In other words, the PCCT apparatus 1 scans the subject P according to the setting in which the partitioning of a plurality of energy ranges is not performed beyond necessity. That enables the PCCT apparatus 1 to hold down an increase in the volume of data while maintaining the accuracy of materials discrimination.

First Modification Example

In the PCCT apparatus 1, the processing circuitry 44 executes computer programs stored in the memory 41 and implements the system control function 4410, the imaging protocol creation function 4420, the list display function 4421, the input function 4422, the acquisition function 4423, the setting function 4424, the setting display function 4425, the adjustment function 4426, the operation function 4427, the details display function 4428, the storage function 4429, the scan control function 4430, the preprocessing function 4440, the reconstruction processing function 4450, and the image display function 4460. However, alternatively, the processing circuitry 44 can implement some or all of the system control function 4410, the imaging protocol creation function 4420, the list display function 4421, the input function 4422, the acquisition function 4423, the setting function 4424, the setting display function 4425, the adjustment function 4426, the operation function 4427, the details display function 4428, the storage function 4429, the scan control function 4430, the preprocessing function 4440, the reconstruction processing function 4450, and the image display function 4460 using hardware such as a semiconductor circuit.

According to at least one embodiment described above, it becomes possible to hold down an increase in the volume of data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the above embodiments, the following notes are presented as certain aspects and optional characteristics of the present disclosure:

(Note 1)

An information processing apparatus that sets an image generation condition for photon counting computed tomography (PCCT) imaging, the information processing apparatus includes:

an input unit that receives an input which specifies a radiogram interpretation target;

an obtaining unit that, based on target-by-target setting information in which, for each radiogram interpretation target, energy range setting is defined which is related to the energy range meant for discriminating the photons originating from the X-rays that have passed through the subject, obtains the energy range setting corresponding to the radiogram interpretation target received by the input unit; and a setting unit that sets the energy range setting obtained by the obtaining unit.

(Note 2)

The information processing apparatus further includes an adjusting unit that, in the target-by-target setting information, adjusts the energy range setting for each radiogram interpretation target.

(Note 3)

The adjusting unit adjusts the number of partitioned energy ranges for each radiogram interpretation target.

(Note 4)

The adjusting unit adjusts the weight coefficient with respect to the energy range for each radiogram interpretation target.

(Note 5)

The adjusting unit includes a details display unit that, in the energy range setting for each radiogram interpretation target, displays at least either the number of partitioned energy ranges or the weight coefficient of the energy range, and an operating unit that receives an operation of changing at least either the number of partitioned energy ranges or the weight coefficient of the energy range as displayed by the details display unit.

(Note 6)

The information processing apparatus further includes a list display unit that displays a radiogram interpretation target list based on the target-by-target setting information, wherein the input unit receives specification of one or more radiogram interpretation targets listed in the radiogram interpretation target list.

(Note 7)

In the radiogram interpretation target list, upon highlighting a first radiogram interpretation target, when a second radiogram interpretation target also gets highlighted, the list display unit displays the first radiogram interpretation target and the second radiogram interpretation target as a single selection option.

(Note 8)

The information processing apparatus further includes a storing unit that stores the energy range setting which has been adjusted by the adjusting unit and which corresponds to the radiogram interpretation target.

(Note 9)

An information processing apparatus that is meant for setting an image generation condition for PCCT imaging, the information processing apparatus including:

an input unit that receives an input which specifies a radiogram interpretation target;

an obtaining unit that, based on target-by-target setting information in which, for each radiogram interpretation target, energy range setting is defined which is related to the an energy range meant for discriminating the photons originating from the X-rays that have passed through the subject, obtains energy range setting corresponding to the radiogram interpretation target received by the input unit;

a setting unit that sets the energy range setting obtained by the obtaining unit;

a setting display unit that displays at least some part of the energy range setting which is set by the setting unit;

an adjusting unit that, in the target-by-target setting information, adjusts the energy range setting for each radiogram interpretation target;

a storing unit that stores the energy range setting which has been adjusted by the adjusting unit and which corresponds to the radiogram interpretation target; and a list display unit that displays a radiogram interpretation target list which includes the energy range setting stored by the storing unit and includes the energy range setting that was already stored.

(Note 10)

A PCCT apparatus includes:

an input unit that receives an input which specifies a radiogram interpretation target;

an obtaining unit that, based on target-by-target setting information in which, for each radiogram interpretation target, energy range setting is defined which is related to the energy range meant for discriminating the photons originating from the X-rays that have passed through the subject, obtains energy range setting corresponding to the radiogram interpretation target received by the input unit;

a setting unit that sets the energy range setting obtained by the obtaining unit; and a data collecting unit that, for each energy range corresponding to the energy range setting that is set by the setting unit, generates, as detection data, a counting result obtained by counting the photons originating from the X-rays that have passed through the subject.

(Note 11)

The energy range setting represents the setting of the number of partitioned energy ranges meant for discriminating the photons originating from the X-rays that have passed through the subject.

(Note 12)

The energy range setting represents the setting of the weight coefficients of the energy ranges meant for discriminating the photons originating from the X-rays that have passed through the subject.

(Note 13)

The radiogram interpretation target represents the body tissues constituting the subject.

(Note 14)

The radiogram interpretation target represents materials constituting the subject.

(Note 15)

When an energy range is selected from among the energy ranges, the operating unit receives an input that specifies the upper limit value and the lower limit value of the selected energy range.

(Note 16)

The operation unit receives an input for increasing the number of partitioned energy ranges.

(Note 17)

The operation unit receives an input for reducing the number of partitioned energy ranges.

(Note 18)

The operation unit receives an input for changing the weight coefficient of the energy range.

(Note 19)

The operation unit receives an input for setting the weight coefficient of the energy range to zero.

(Note 20)

The PCCT apparatus further includes:

a reconstructing unit that performs reconstruction processing with respect to projection data, which is obtained as a result of scanning the subject, according to the changed weight coefficient of the energy range as changed by the operating unit; and an image display unit that displays CT image data.

What is claimed is:

1. An information processing apparatus that sets an image generation condition for photon counting computed tomography (PCCT) imaging, the information processing apparatus comprising:

processing circuitry configured to receive an input which specifies a radiogram interpretation target from a list of radiogram interpretation targets, from target-by-target setting information in which, for each radiogram interpretation target, a corresponding energy range setting is defined that is related to an energy range meant for discriminating photons originating from X-rays that have passed through a subject, obtain an energy range setting corresponding to the radiogram interpretation target that is specified by the input received, and set the obtained energy range setting.

2. The information processing apparatus according to claim 1, wherein the processing circuitry is further configured to adjust, in the target-by-target setting information, the corresponding energy range setting for each of the radiogram interpretation targets.

3. The information processing apparatus according to claim 2, wherein the processing circuitry is further configured to adjust a number of partitions of the energy range for each of the radiogram interpretation targets.

4. The information processing apparatus according to claim 2, wherein the processing circuitry is further configured to adjust a weight coefficient with respect to the energy range for each of the radiogram interpretation targets.

5. The information processing apparatus according to claim 2, wherein the processing circuitry is further configured to:

display, in the corresponding energy range setting for each of the radiogram interpretation targets, at least either a number of partitions of the energy range or a weight coefficient of the energy range, and receive an operation of changing at least either the displayed number of the partitions of the energy range or the displayed weight coefficient of the energy range.

6. The information processing apparatus according to claim 1, wherein the processing circuitry is further configured to;

display the list of the radiogram interpretation targets based on the target-by-target setting information, and receive a specification of one or more of the radiogram interpretation targets listed in the list of the radiogram interpretation list targets.

7. The information processing apparatus according to claim 6, wherein, in the list of the radiogram interpretation list targets, upon highlighting a first radiogram interpretation target, when a second radiogram interpretation target also gets highlighted, the processing circuitry is further configured to display the first radiogram interpretation target and the second radiogram interpretation target as a single selection option.

8. The information processing apparatus according to claim 2, wherein the processing circuitry is further configured to store the corresponding energy range setting which has been adjusted and which corresponds to the specified radiogram interpretation target.

9. An information processing apparatus to set an image generation condition for PCCT imaging, the information processing apparatus comprising:

processing circuitry configured to receive an input which specifies a radiogram interpretation target from a list of radiogram interpretation targets, from target-by-target setting information in which, for each radiogram interpretation target, a corresponding energy range setting is defined that is related to an energy range meant for discriminating photons originating from X-rays that have passed through a subject, obtain an energy range setting corresponding to the radiogram interpretation target that is specified by the input received, set the obtained energy range setting, display at least some part of the energy range setting that has been set, adjust, in the target-by-target setting information, the corresponding energy range setting for each of the radiogram interpretation target, store the energy range setting that has been adjusted and that corresponds to the specified radiogram interpretation target, and display the list of the radiogram interpretation targets, which includes the energy range setting that is stored and includes the energy range setting that was already stored.

* * * * *